United States Patent [19]

Sappelt

[11] 4,394,521
[45] Jul. 19, 1983

[54] PROCESS FOR THE PRODUCTION OF THE SCHIFF'S BASES OF 2,6-DICHLORO-5-HYDROXY-ANILINE

[75] Inventor: Reinhard Sappelt, Meersburg, Fed. Rep. of Germany

[73] Assignee: Lonza-Werke G.m.b.H., Weil am Rhein, Fed. Rep. of Germany

[21] Appl. No.: 258,522

[22] Filed: Apr. 28, 1981

[51] Int. Cl.$^3$ ............................................. C07C 119/10
[52] U.S. Cl. ...................................... 564/271; 564/442
[58] Field of Search ................................ 564/271, 442

[56] References Cited

U.S. PATENT DOCUMENTS 2,218,587 10/1940 Reddelien ........................... 564/271
2,513,996  7/1954 Haury ............................. 564/271 X
2,692,284 10/1954 Haury ............................. 564/271 X
3,135,796  6/1964 Layer et al. ......................... 564/271
3,414,616 12/1968 Summers ............................ 564/271
4,281,195  7/1981 George .............................. 564/271

FOREIGN PATENT DOCUMENTS 803199 10/1958 United Kingdom ................. 564/271

OTHER PUBLICATIONS

Roberts et al., "Basic Principles of Organic Chemistry", pp. 449-453 (1964).
Groves et al., "Chemical Abstracts", vol. 23, p. 2957 (1929).
Bray et al., "Chemical Abstracts", vol. 51, pp. 7564-7565 (1957).

Primary Examiner—Robert V. Hines
Attorney, Agent, or Firm—Fisher, Christen & Sabol

[57] ABSTRACT

Process for the production of 2,6-dichloro-5-hydroxy-anils having the formula:

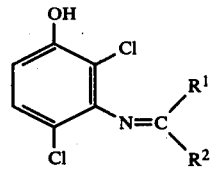

wherein $R^1$ and $R^2$ are the same or different and each is an alkyl radical having 1 to 4 carbon atoms, by the conversion of 2,4-dichloro-3-aminophenol with a ketone. The reaction is conducted at a temperature of 0° to 50° C.

25 Claims, No Drawings

PROCESS FOR THE PRODUCTION OF THE SCHIFF'S BASES OF 2,6-DICHLORO-5-HYDROXY-ANILINE

FIELD OF THIS INVENTION

This invention relates to a process for the production of 2,6-dichloro-5-hydroxy-anils having the formula:

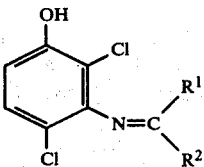

wherein $R^1$ and $R^2$ are the same or different entity and each is an alkyl radical having 1 to 4 C atoms.

BROAD DESCRIPTION OF THIS INVENTION

An object of this invention is to provide a process for the production of 2,6-dichloro-5-hydroxy-anils, particularly from a mixture of chloroamines obtained from the chlorination of 3-nitrophenol. Other objects and advantages of this invention are set out herein or are obvious herefrom to one ordinarily skilled in the art.

The objects and advantages of this invention are achieved by the process of this invention.

This invention involves the production of 2,6-dichloro-5-hydroxy-anils [also termed 1-hydroxy-2,4-dichloro-N-(akylidene)-aniline-3] having the formula:

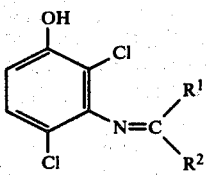

wherein $R^1$ and $R^2$ are the same or different moiety and each is an alkyl radical having 1 to 4 C atoms. According to this invention such compounds are produced by a reaction of 2,4-dichloro-3-amino-phenol with at least one compound having the formula:

wherein $R^1$ and $R^2$ are the same or different and each is an alkyl radical having 1 to 4 C atoms. Preferably the 2,4-dichloro-3-amino-phenol is part of a mixture of chlorinated aminophenols.

The compounds produced by the process of this invention are useful as coupling components for the production of dyestuffs.

Compounds having the formula $R^1$—CO—$R^2$ are for example ketones, such as, acetone, methyl ethyl ketone, isobutyl ketone, 2-pentanone, 3-methyl-2-butanone, 3-pentanone, 2-hexanone, 3-hexanone, methyl isobutyl ketone, 2-methyl-3-pentanone, 3-methyl-2-pentanone, methyl t-butyl ketone, dipropyl ketone, diisopropyl ketone, di-isobutyl ketone and hexamethylacetone.

The compounds of the formula $R^1$—CO—$R^2$ are preferably used in an excess (for example, up to 20 or so moles per mole of the 2,4-dichloro-3-amino-phenol), whereby at the same time they serve as solvent and reactant. The process of this invention can also be carried out in the presence of other solvents such as alcohols, e.g., methanol, ethanol, butanol, isopropanol, propanol and isobutanol, or chlorinated hydrocarbons, e.g., carbon tetrachloride, 1,2-dichloroethane, 1-chlorobutane, 2-chlorobutane, 1,1-dichloroethane, 1,1,2,2-tetrachloroethane, 1,1,1,2-tetrachloroethane, 1,4-dichlorobutane, 2,2-dichlorobutane, 2,3-dichlorobutane, 1-chloropropane, pentachloroethane, 1,1,1-trichloroethane, 1-chloropentane, 1,1,2-trichloroethane, 1,1-dichlorobutane, 1,2-dichlorobutane, 1,3-dichlorobutane, 1,1,1,2-tetrachlorobutane, 1,2-dichloropropane, 1,3-dichloropropane, 2,2-dichloropropane, 1,1,3-trichloropropane, 1,1,1,2-tetrachloropropane and 2-chloropentane.

The reaction is carried out effectively in the presence of at least one catalyst which favors separation of water. Such catalysts are advantageously mineral acids, such as HCl and $H_2SO_4$, as well as toluenesulfonic acid and others. HCl is the preferred catalyst.

The temperature used during the reaction is between 0° and 50° C. and preferably from 6° to 12° C.

The most advantageous way to produce the Schiff's bases of 2,6-dichloro-5-hydroxy-aniline is that which starts out with the chloroamine mixture obtained by the chlorination of 3-nitrophenol and subsequent reduction of the nitro group. Such mixture always contains about one-third 2,4-dichloro-3-aminophenol, about one third 4,6-dichloro-3-aminophenol and one third 2,4,6-trichloro-3-aminophenol. Surprisingly, it turned out that only the 2,4-dichloro-3-aminophenol is converted and forms the desired base corresponding to Schiff.

The process of this invention can be considered as a separation process for the separation of 2,4-dichloro-3-aminophenol from the chloroamine mixture.

The chlorination of 3-nitrophenol is carried out effectively with elementary chlorine in the melt in the temperature range of 60° to 100° C., preferably at 70° to 90° C., or in a halogenated solvent, such as, chloroform carbon tetrachloride, tetrachloroethane, 1,1,2-trichlorofluorethane and o-dichlorobenzol, at the boiling temperature of the solvent, preferably at 50° C.

The chlorination can also be carried out in water in the presence of an emulsifier or in the presence of acetic acid at a temperature of 40° to 90° C., preferably at 50° to 80° C.

DETAILED DESCRIPTION OF THIS INVENTION

EXAMPLE 1

4200 g of the chloroamine mixture is dissolved in 10 l of acetone, and is cooled to and kept under cooling at 8° to 10° C. During a period of 6½ hours, 1000 g of HCl gas is introduced into the solution. Subsequently, the material is reacted for an additional 3 hours and the precipitated crystals are only then sucked off. The filter cake, which has a strong reddish brown color, is suspended in acetone, is sucked off and subsequently is washed three times with 500 ml of acetone (i.e., altogether with 1.5 l of acetone). This is immediately sucked off and pressed out, so that the filter cake is largely freed of the acetone. The yield, after drying in the vacuum, amounts to 1000 g of 2,6-dichloro-5-hydroxy-N-(isopropylidene)-aniline.HCl having a melting point of from 177° to 179° C.

The identification is accomplished by means of NMR-spectroscopy.

EXAMPLE 2

4200 g of the chloroamine mixture is dissolved in 10 l of methyl ethyl ketone, and is cooled to and kept under cooling at 8° to 10° C. During a period of 6½ hours, 1000 g of HCl gas is introduced into the solution. Subsequently, the material is allowed to react again for another 3 hours and the precipitated crystals only then are sucked off. The filter cake, which has a strong reddish brown coloration, is suspended in methyl ethyl ketone, is sucked off and is washed again three times, each time with 500 ml of methyl ethyl ketone (i.e., altogether with 1.5 l of methyl ethyl ketone). This is immediately sucked off and pressed out, so that the filter cake is largely freed of methyl ethyl ketone. The yield, after drying in the vacuum, amounts to 1080 g of 2,6-dichloro-5-hydroxy-N-(butylidene-3)-aniline.HCl having a melting point of 172° to 173° C.

The identification is made by means of NMR-spectroscopy.

What is claimed is:

1. Process for the production of 2,6-dichloro-5-hydroxy-anils having the formula:

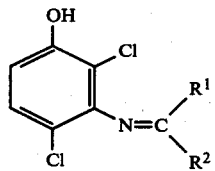

wherein R¹ and R² are the same or different and each is an alkyl radical having 1 to 4 C atoms, comprising reacting 2,4-dichloro-3-aminophenol with a ketone having the formula:

wherein R¹ and R² have the same meaning as above.

2. Process for the production of 2,6-dichloro-5-hydroxy-anils as claimed in claim 1 wherein said 2,4-dichloro-3-aminophenol is used in the form of a component in a mixture of chlorinated aminophenols.

3. Process for the production of 2,6-dichloro-5-hydroxy-anils as claimed in claim 2 wherein the reaction is carried out at temperatures from 0° to 50° C.

4. Process for the production of 2,6-dichloro-5-hydroxy-anils as claimed in claim 2 wherein the reaction is conducted at a temperature from 6° to 12° C.

5. Process for the production of 2,6-dichloro-5-hydroxy-anils as claimed in claim 2 wherein a catalyst is present.

6. Process for the production of 2,6-dichloro-5-hydroxy-anils as claimed in claim 5 wherein said catalyst is a mineral acid.

7. Process for the production of 2,6-dichloro-5-hydroxy-anils as claimed in claim 5 wherein said catalyst is HCl.

8. Process for the production of 2,6-dichloro-5-hydroxy-anils as claimed in claim 2 wherein a solvent is present.

9. Process for the production of 2,6-dichloro-5-hydroxy-anils as claimed in claim 8 wherein the product is recovered from the solvent as precipitated crystals.

10. Process for the production of 2,6-dichloro-5-hydroxy-anils as claimed in claim 8 wherein the solvent is methanol, ethanol, butanol, isopropanol, propanol, isobutanol, carbon tetrachloride, 1,2-dichloroethane, 1-chlorobutane, 2-chlorobutane, 1,1-dichloroethane, 1,1,2,2-tetrachloroethane, 1,1,1,2-tetrachloroethane, 1,4-dichlorobutane, 2,2-dichlorobutane, 2,3-dichlorobutane, 1-chloropropane, pentachloroethane, 1,1,1-trichloroethane, 1-chloropentane, 1,1,2-trichloroethane, 1,1-dichlorobutane, 1,2-dichlorobutane, 1,3-dichlorobutane, 1,1,1,2-tetrachlorobutane, 1,2-dichloropropane, 1,3-dichloropropane, 2,2-dichloropropane, 1,1,3-trichloropropane, 1,1,1,2-tetrachloropropane or 2-chloropentane.

11. Process for the production of 2,6-dichloro-5-hydroxy-anils as claimed in claim 10 wherein up to 20 moles of said ketone is used per mole of 2,4-dichloro-3-aminophenol.

12. Process for the production of 2,6-dichloro-5-hydroxy-anils as claimed in claim 8 wherein said solvent is an alcohol or a chlorinated hydrocarbon.

13. Process for the production of 2,6-dichloro-5-hydroxy-anils as claimed in claim 2 wherein said mixture of chlorinated aminophenols comprises 2,4-dichloro-3-aminophenol, 4,6-dichloro-3-aminophenol and 2,4,6-trichloro-3-aminophenol.

14. Process for the production of 2,6-dichloro-5-hydroxy-anils as claimed in claim 2 wherein the compound having the formula R¹—CO—R² is acetone.

15. Process for the production of 2,6-dichloro-5-hydroxy-anils as claimed in claim 2 wherein the mixture of chlorinated aminophenols was prepared by chlorinating 3-nitrophenol with elemental chlorine in a melt at a temperature of 60° to 100° C. or in a halogenated solvent, such as chloroform carbon tetrachloride, tetrachloroethane, 1,1,2-trichlorofluorethane and o-dichlorobenzol, at the boiling temperature of the solvent, or in water in the presence of an emulsifier or in the presence of acetic acid at a temperature of 40° to 90° C., and then reducing the nitro group of the chlorinated nitrophenol.

16. Process for the production of 2,6-dichloro-5-hydroxy-anils as claimed in claim 2 wherein the compound having the formula R¹—CO—R² is methyl ethyl ketone.

17. Process for the production of 2,6-dichloro-5-hydroxy-anils as claimed in claim 1 wherein the ketone having the formula R¹—CO—R² is acetone, methyl ethyl ketone, isobutyl ketone, 2-pentanone, 3-methyl-2-butanone, 3-pentanone, 2-hexanone, 3-hexanone, methyl isobutyl ketone, 2-methyl-3-pentanone, 3-methyl-2-pentanone, methyl t-butyl ketone, dipropyl ketone, diisopropyl ketone, diisobutyl ketone or hexamethylacetone.

18. Process for the production of 2,6-dichloro-5-hydroxy-anils as claimed in any of claims 1 to 7 and 13 to 16 wherein an excess of said ketone is used.

19. Composition comprising a mixture of 2,4-dichloro-3-aminophenol and a ketone having the formula:

wherein R¹ and R² are the same or different and each is an alkyl radical having 1 to 4 C atoms.

20. Composition as claimed in claim 19 wherein the ketone having the formula R¹—CO—R² is acetone, methyl ethyl ketone, isobutyl ketone, 2-pentanone, 3-methyl-2-butanone, 3-pentanone, 2-hexanone, 3-hexanone, methyl isobutyl ketone, 2-methyl-3-pentanone, 3-methyl-2-pentanone, methyl t-butyl ketone, dipropyl ketone, diisopropyl ketone, diisobutyl ketone or hexamethylacetone.

21. Composition as claimed in claim 19 wherein an acid catalyst, a solvent, 4,6-dichloro-3-aminophenol and 2,4,6-trichloro-3-aminophenol are also present.

22. Composition as claimed in claim 21 wherein the solvent is methanol, ethanol, butanol, isopropanol, propanol, isobutanol, carbon tetrachloride, 1,2-dichloroethane, 1-chlorobutane, 1,1-dichloroethane, 1,1,2,2-tetrachloroethane, 1,1,1,2-tetrachloroethane, 1,4-dichlorobutane, 2,2-dichlorobutane, 2,3-dichlorobutane, 1-chloropropane, pentachloroethane, 1,1,1-trichloroethane, 1-chloropentane, 1,1,2-trichloroethane, 1,1-dichlorbutane, 1,2-dichlorobutane, 1,3-dichlorobutane, 1,1,1,2-tetrachlorobutane, 1,2-dichloropropane, 1,3-dichloropropane, 2,2-dichloropropane, 1,1,3-trichloropropane, 1,1,1,2-tetrachloropropane or 2-chloropentane.

23. Composition as claimed in claim 21 wherein said acid catalyst is a mineral acid.

24. Composition as claimed in claim 23 wherein said catalyst is HCl or $H_2SO_4$.

25. Composition as claimed in claim 21 wherein said solvent is an alcohol or a chlorinated hydrocarbon.

* * * * *

UNITED STATES PATENT OFFICE
CERTIFICATE OF CORRECTION

Patent No. 4,394,521                    Dated   July 19, 1983

Inventor(s)  Sappelt

It is certified that error appears in the above-identified patent and that said Letters Patent are hereby corrected as shown below:

On the title page add:  [30] Foreign Application Priority Data
    April 30, 1980   Switzerland ................. 3331/80

Signed and Sealed this

*Eighteenth* Day of *October 1983*

[SEAL]

*Attest:*

*Attesting Officer*

GERALD J. MOSSINGHOFF

*Commissioner of Patents and Trademarks*